United States Patent
Li et al.

(10) Patent No.: US 10,278,978 B2
(45) Date of Patent: May 7, 2019

(54) HUMAN LUNG TISSUES-ACTIVE TARGETING IMMUNE NANOLIPOSOME OF METHYLPREDNISOLONE AND A METHOD FOR PRODUCING THE SAME

(71) Applicant: Shanghai Pulmonary Hospital, Shanghai (CN)

(72) Inventors: Huiping Li, Shanghai (CN); Zhaofang Yin, Shanghai (CN); Xian He, Shanghai (CN); Shanmei Wang, Shanghai (CN)

(73) Assignee: SHANGHAI PULMONARY HOSPITAL, Shanghai (CN)

( * ) Notice: Subject to any disclaimer, the term of this patent is extended or adjusted under 35 U.S.C. 154(b) by 183 days.

(21) Appl. No.: 15/026,219

(22) PCT Filed: Nov. 27, 2015

(86) PCT No.: PCT/CN2015/095727
§ 371 (c)(1),
(2) Date: Mar. 30, 2016

(87) PCT Pub. No.: WO2017/080002
PCT Pub. Date: May 18, 2017

(65) Prior Publication Data
US 2017/0258811 A1    Sep. 14, 2017

(30) Foreign Application Priority Data
Nov. 9, 2015  (CN) .......................... 2015 1 0759596

(51) Int. Cl.
*A61K 31/573* (2006.01)
*A61K 9/127* (2006.01)
*A61K 9/00* (2006.01)
*A61K 47/68* (2017.01)
*A61K 47/69* (2017.01)

(52) U.S. Cl.
CPC .......... *A61K 31/573* (2013.01); *A61K 9/0019* (2013.01); *A61K 9/1271* (2013.01); *A61K 9/1277* (2013.01); *A61K 47/6843* (2017.08); *A61K 47/6913* (2017.08)

(58) Field of Classification Search
None
See application file for complete search history.

(56) References Cited

U.S. PATENT DOCUMENTS

| 9,228,010 B2 * | 1/2016 | Li | ........................... C07K 16/18 |
| 2014/0314832 A1 * | 10/2014 | Li | ........................... C07K 16/18 424/450 |

FOREIGN PATENT DOCUMENTS

CN   103705470   *   1/2014   ............... A61K 9/14

OTHER PUBLICATIONS

Guo, D. et al., "Coupling of Liposome Phosphatide and Antibody Protein", Journal of South China University of Technology (Natural Science) vol. 33, No. 03, Mar. 28, 2005.
PCT International Search Report, PCT/CN2015/095727, dated Jul. 7, 2016.

* cited by examiner

*Primary Examiner* — Yunsoo Kim
(74) *Attorney, Agent, or Firm* — Fish IP Law, LLP

(57) ABSTRACT

Present invention relates to a human lung tissues-active targeting immune nanoliposome of methylprednisolone, wherein, nanoliposomes loaded with therapy drugs is covalently coupled with nanobodies against human pulmonary surfactant protein A. Wherein, the therapy drug is methylprednisolone sodium succinate, the nanoliposome consists of phospholipids, cholesterols and long cycling materials. The molar ratio of the methylprednisolone sodium succinate to phospholipids within the nanoliposome is 0.30-0.45. Present invention successfully provides a new human lung tissues targeting hormone preparation, wherein, the nanoliposome serves as a carrier, the nanobody against human pulmonary surfactant protein A serves as a specific lung tissue targeting ligand, methylprednisolone sodium succinate serves as a therapy drug. In accordance with present invention, an efficient, stable human lung tissues-active targeting immune nanoliposome, with specific active lung targeting, is prepared.

9 Claims, 6 Drawing Sheets

HUMAN LUNG TISSUES-ACTIVE TARGETING IMMUNE NANOLIPOSOME OF METHYLPREDNISOLONE AND A METHOD FOR PRODUCING THE SAME

This application is a U.S. National Phase of PCT/CN2015/095727, filed on Nov. 25, 2015, which claims the benefit of priority to Chinese Patent Application No. 201510759596.8, filed Nov. 9, 2015.

FIELD OF THE INVENTION

The present invention relates to the field of pharmaceutical preparation, particularly to a human lung tissues-active targeting immune nanoliposome of methylprednisolone and a method for producing the same.

BACKGROUND OF THE INVENTION

The existing technology discloses that glucocorticoid drugs provide remarkable anti-inflammatory effect, immunosuppressive effect and antishock effect, thus they are widely applied to clinical diseases therapy. Glucocorticoid drugs are also most commonly used drugs applied on treating diseases of respiratory system, such as bronchial asthma, chronic obstructive pulmonary disease, interstitial lung disease, acute lung injury (ALI), pulmonary vasculitis, acute respiratory distress syndrome (ARDS) and so on. Wherein, treatment of some diseases such as bronchial asthma, sarcoidosis need long-term administration of the hormone. However, glucocorticoid drugs are medicine with quite obvious adverse drug reaction, which often results in a series of side effects, for example, anaphylactic reaction, hyperglycemia, hypertension, peptic ulcer, gastrointestinal bleeding, osteoporosis, Cushing syndrome, which may make patients physically disabled or even be life-threatening in severe patients. Therefore, it is an important issue which must be solved on the clinical and basic research that how to reduce glucocorticoid drugs concentration in non-treated areas to avoid adverse drug reaction for maximizing therapeutic effect.

In recent years, the rapid development of targeting nanotechnology brings new hope to solve the medical problem. Nanotechnology has been successfully applied in many technical fields, wherein, nano-drug delivery system based on the nanotechnology becomes one of the major developmental tendencies of modern medicine. Compared to ordinary dosage forms, the nanostructure of medicine provides bigger specific surface area, higher chemical activity and faster absorption rate, prolongs therapeutic drug level, lowers the risk of adverse drug reaction and improves medicine curative effect. On research of setting the target activity of medicine, nano-drug carrier with targeting becomes a research focus on nanotechnology and medicine controlled-release technique. The nano-drug carrier with targeting has characteristics of controlling drug release according to physical and psychological needs so as to form a drug delivery system in nanoscale. Based on different stimulus signals, the drug delivery system can be classified as a physical signal stimuli responsive drug delivery system, a chemical signal stimuli responsive drug delivery system and a biological signal stimuli responsive drug delivery system. Biological target therapy comprises: as utilization of antibody, with the help of specificity effect of cell membrane surface receptor or particular gene segment, the ligand is bonded to the carrier, then it is specifically bonded to an antigenicity recognizer on the surface of the target cell by the action of the promoter, so that the drugs are delivered to target cells precisely, for implementing target therapy.

In 1993, Hamers-Casterman etc. first reported the existence of a natural heavy chain antibody (HCAbs) lacking of light chain in camel blood. The variable region of the natural heavy chain antibody separately forms a complete antigen binding sites, whose scale is nanoscale, so the antibody is also known as the nanobody (Nbs). Study result shows that said antibody has lots of peculiar properties such as excellent stability, high affinity, weak immunogenicity, strong tissues penetration and so on superior to ordinary antibodies. Therefore, it has a vast potential for future development in the field of medicine.

Existing research shows that using type II pneumonocyte as a target could carry out targeting transportation of lung tissue drugs. Type II pneumonocyte is exclusively contained in lung tissues, and it is one sort of cell which has the function of proliferation and secretion, its amount is about 16% of the total lung parenchymal cells, with the function of synthesizing and secreting pulmonary surfactants. The pulmonary surfactants, which are composed primarily of lipids (90%) and proteins (10%), are stored in the lamellar body within a cell, then said pulmonary surfactants could be secreted in alveolar spaces for producing physiological effects. The protein component in the pulmonary surfactant is the specific surfactant protein (SP), which is named SP-A, SP-B, SP-C, SP-D according to the order it is discovered. Wherein, SP-A is a hydrophilic glycoprotein, consisting of 248 amino acids, and SP-A is the earliest protein with a strong signal and being strongly expressed in type H pneumonocyte found by human being. The study found that, it could keep a high concentration of SP-A expression in lung and an extremely low concentration of SP-A extrapulmonary expression, so SP-A has lung specificity and becomes an ideal lung-specific targeting molecule. In conclusion, it is achievable that glucocorticoids are targeting transported to human lung tissues as long as the specific nano-drug carriers are loaded with glucocorticoids and then are coupled with nanobodies against human pulmonary surfactant protein A.

The applicant has successfully developed a rat pulmonary targeting immune liposome of methylprednisolone previously (Application Number: CN201510334884.9). It possesses definite rat pulmonary targeting and efficiently and stably carries out targeting transportation of active pharmaceutical ingredient to rat lung tissues. The lung tissue targeting ligand used in the invention is the murine SP-A nanobody (SPANb) self-developed by present R&D team (Application Number: CN201310134673.1). Recently, present R&D team further has successfully developed the humanized SP-A nanobody (Application Number: CN201510086499.7). Based on above studies made by present R&D team, this invention successfully provides a new human lung tissues targeting hormone preparation, with the final purpose of maximizing drug therapeutic effect while minimizing the adverse drug reaction by clinically using this new preparation, with high efficiency and low toxicity, in the treatment of human pulmonary diseases.

SUMMARY OF THE INVENTION

Based on above preliminary studies, present invention utilizes methylprednisolone as the therapy drug and uses self-developed humanized SP-A nanobody as new targeted ligand for SP-A, then the nanobody is coupled with drug loaded liposome, finally, a human lung tissues-active targeting immune nanoliposome of methylprednisolone is prepared.

In accordance with the first aspect of the present invention, a human lung tissues-active targeting immune nanoliposome of methylprednisolone is provided. The nanoliposome consists of nanobodies against human pulmonary surfactant protein A, nano lipids and therapy drugs. Specifically, the human lung tissues-active targeting immune liposome of methylprednisolone according to present invention includes nanoliposomes, which are loaded with therapy drugs, covalent coupling nanobodies against human pulmonary surfactant protein A; wherein, the therapy drug is methylprednisolone sodium succinate, the nanoliposome comprises phospholipids, cholesterols and long cycling materials. The molar ratio of the methylprednisolone sodium succinate to phospholipids within the nanoliposome is 0.30-0.45.

According to present invention, the nanoliposome comprises phospholipids, cholesterols and long cycling materials. Wherein, the phospholipid is distearoyl phosphatidylcholine (DSPC), said long cycling material includes DSPE-$PEG_{2000}$, DSPE-$PEG_{2000}$-COOH.

In this invention, for preparing the nanoliposome, the molar ratio of used phospholipid:cholesterol:DSPE-$PEG_{2000}$:DSPE-$PEG_{2000}$-COOH is 20:14.5:1.8:0.05. Finally, the molar ratio of nanobodies against human pulmonary surfactant protein A to DSPE-$PEG_{2000}$-COOH is 1:70.

In this invention, the therapy drug is chosen from methylprednisolone sodium succinate, which belongs to glucocorticoid and has weak acidity and amphipathy. Medicine carrying by the lipidosome is implemented by means of active loading method in pH gradient. The molar ratio of the therapy drug to phospholipids within the nanoliposome is 0.30-0.45, preferably, 0.40.

In this invention, the immune nanoliposome of methylprednisolone is entirely spherical in shape, with average particle size of 119.1±0.2 nm; the entrapment rate of the nanoliposome to active pharmaceutical ingredients in therapy drugs is 89.7±0.1%.

In accordance with the second aspect of present invention, a method for producing the human lung tissues-active targeting immune nanoliposome of methylprednisolone is provided, comprising the steps of:

Step 1): preparation of the nanoliposome of methylprednisolone (MPS-NSSLs)

A film-ultrasonic technique is employed for preparing the nanoliposome of methylprednisolone, using phospholipid, cholesterol, DSPE-$PEG_{2000}$, DSPE-$PEG_{2000}$-COOH as film-forming materials;

Step 2): preparation of the nanoliposome of methylprednisolone coupled with nanobodies against human pulmonary surfactant protein a (MPS-NSSLs-SPANb);

Step 3): characterization of the nanoliposome of methylprednisolone coupled with nanobodies against human pulmonary surfactant protein A (MPS-NSSLs-SPANb): shape, particle size, entrapment rate and stability; connection verification of the nanoliposome of methylprednisolone and nanobodies against human pulmonary surfactant protein a and activity detection of them.

According to present invention, concrete steps of the preparation method and verification experiments are as follows:

Step 1. Preparation of the nanoliposome of methylprednisolone (MPS-NSSLs)

A film-ultrasonic technique is employed for preparing the nanoliposome of methylprednisolone. The mixed solvent of chloroform/methanol (the volume ratio is 2:1) is used to dissolve respectively weighed distearoyl phosphatidylcholine (DSPC), cholesterol and DSPE-PEG2000 (the molar ratio of each component is 20:14.5:1.8) with formula dosage in a round-bottom flask. After dried under nitrogen, a membrane with even thickness glued to the wall of the round-bottom flask is formed. The membrane is vacuum dried overnight at room temperature, for removing any organic solvent. A moderate amount of calcium acetate solution (concentration is 200 mM) is used for hydration, then an ultrasound bath in 72° C. is used to dissolve lipidosomes (ultrasonic processing in 30 mins, with ultrasonic power of 250 W), thus mid blue opalescence solution is obtained. Sequentially, the ultrasound-treated hydration solution runs through three filter membranes with pore size of 0.4 μm, 0.2 μm, 0.1 μm in sequence, by means of the Lipidosome Extruder (Avanti® Mini-Extruder), extruded 13-17 times in each level, and then lipidosome suspension is obtained. The obtained lipidosome suspension is dialyzed in the dialysis tube (molecular weight of 300 kDa) containing 0.9% normal saline overnight. Methylprednisolone sodium succinate (MPS) with formula dosage is weighed and dissolved in 0.9% normal saline for preparing MPS solution with molarity of 4.2 mM. The MPS solution is mixed with the lipidosome suspension (concentration of phospholipids is 14.3 mM), then the mixture is heated in water bath at 70° C. for 40 mins, at last, it is stored at 4° C. Free MPS, which is not encapsulated, is removed with the help of gel filtration chromatography (Superose G-25).

Step 2. Characterization of the nanoliposome of methylprednisolone (MPS-NSSLs)

Appearance of MPS-NSSL shows entirely spherical in shape, with even size (see FIG. 1A);

The average particle size of MPS-NSSL is 108.4±0.4 nm (see FIG. 2A);

The entrapment rate of MPS-NSSL: the entrapment rate of the nanoliposome of methylprednisolone to methylprednisolone sodium succinate is 90.1±0.32%;

Step 3. Preparation of the nanoliposome of methylprednisolone coupled with nanobodies against human pulmonary surfactant protein A (MPS-NSSLs-SPANb)

Firstly, the liposome containing DSPE-$PEG_{2000}$-COOH is prepared, and the carboxyl on the surface of the liposome is utilized to make coupling reaction with amidogens in nanobodies against human pulmonary surfactant protein A (FIG. 3 shows the basic reaction mechanism).

A film-ultrasonic technique is employed for using phospholipid, cholesterol, DSPE-$PEG_{2000}$, DSPE-$PEG_{2000}$-COOH as film-forming materials to prepare the nanoliposome of methylprednisolone containing DSPE-$PEG_{2000}$-COOH. The preparation process of it is the same as the preparation process of the nanoliposome of methylprednisolone containing MPS-NSSLs.

An aqueous solution of 120 μL 0.25 mol/L 1-ethyl-3-(3-dimethylaminopropyl) carbodiimide (EDC) and 120 μL 0.25 mol/L N-hydroxysulfosuccinimide (S-NHS) is added into 150 μL liposome suspension (MES buffer solution, pH 4~5.5, total molar quantity of the liposome is 3 μmol) containing DSPE-$PEG_{2000}$-COOH.

The mixture is incubated for 15 min at room temperature, then using NaOH to neutralize to pH 7.5.

The nanobody against human pulmonary surfactant protein A is added to the activated liposome and blended (the molar concentration ratio of DSPE-$PEG_{2000}$-COOH and the nanobody against human pulmonary surfactant protein A is 70:1). The obtained mixture is stirred gently at 4° C. and keeps the temperature, reacting for 8 h. Sepharose CL-4B column pretreated by buffer solution is used to separate the immune liposome from unconnected antibody.

Step 4. Characterization of the nanoliposome of methylprednisolone coupled with nanobodies against human pulmonary surfactant protein A (MPS-NSSLs-SPANb) and coupling verification of them.

The nanoliposome of methylprednisolone coupled with nanobodies against human pulmonary surfactant protein A is entirely spherical in shape, with even size (see FIG. 1B);

The average particle size of the nanoliposome of methylprednisolone coupled with nanobodies against human pulmonary surfactant protein A is 119.1±0.2 nm (see FIG. 2B);

The entrapment rate of the nanoliposome of methylprednisolone coupled with nanobodies against human pulmonary surfactant protein A to methylprednisolone sodium succinate is 89.7±0.1%;

The nanoliposome of methylprednisolone coupled with nanobodies against human pulmonary surfactant protein A is stored for 12 weeks at 4° C., but the entrapment rate of the nanoliposome to methylprednisolone sodium succinate has no significant changes (p>0.05), and the samples are stably stored (as shown in the Table 1 below):

TABLE 1

| Stability detection of MPS-NSSLs-SPANb | |
|---|---|
| Time | Encapsulation Efficiency(%) |
| 0 w | 89.7 ± 0.1 |
| 4 w | 87.0 ± 1.1 |
| 8 w | 85.6 ± 1.7 |
| 12 w | 83.7 ± 3.1 |

The polyacrylamide gel electrophoretic analysis (SDS-PAGE) of the nanoliposome of methylprednisolone coupled with nanobodies against human pulmonary surfactant protein A shows that the nanoliposome of methylprednisolone has successfully coupled with human pulmonary surfactant protein A, because of the increasing of molecular mass which equals to the original molecular mass of human pulmonary surfactant protein A added the molecular mass of the liposome (see FIG. 4).

After nanobodies against human pulmonary surfactant protein A coupled with the nanoliposome of methylprednisolone, Sepharose CL-4B column purification is applied. Then, the human pulmonary surfactant protein A as antigens is used for ELISA detection technology, which shows that the nanoliposome of methylprednisolone coupled with nanobodies against human pulmonary surfactant protein A has better activity for binding to the human pulmonary surfactant protein A as antigens compared with simple nanoliposome of methylprednisolone, p<0.05; the nanoliposome of methylprednisolone coupled with nanobodies against human pulmonary surfactant protein A has little difference of activity for binding to the human pulmonary surfactant protein A as antigens from nanobodies against human pulmonary surfactant protein A, p>0.05 (see FIG. 5).

Step 5. Human lung tissues targeting test of the immune nanoliposome of mthylprednisolone (MPS-NSSLs-SPANb) coupled with nanobodies against human pulmonary surfactant protein A Fresh lung tissues and organs are used as targets for immunohistochemistry staining. It turned out that both the nanobodies against human pulmonary surfactant protein A and the nanoliposome of methylprednisolone coupled with nanobodies against human pulmonary surfactant protein A have been obviously combined with human lung tissues (shown in brown), wherein, the combining capacity of the nanoliposome of methylprednisolone coupled with nanobodies against human pulmonary surfactant protein A is similar to that of the nanobodies against human pulmonary surfactant protein A. However, it is not observed that any of them is obviously combined with human liver, spleen and kidney tissues. As a result, we can find that the nanoliposome of methylprednisolone coupled with nanobodies against human pulmonary surfactant protein A possesses specificity for lung targeting (see FIG. 6).

Step 6. Living imaging of small animals for real-time observation of metabolism of MPS-NSSLs-SPANb in vivo 5 nude mice in 2 weeks old are selected and divided into five groups, wherein, the group treated by the lung targeting liposome of methylprednisolone (MPS-NSSLs-SPANb-FITC) and the group treated by the lung targeting liposome without loading drugs (NSSLs-SPANb-FITC) are experimental groups, the group treated by FITC labeled lung SP-A nanobodies (SPANb-FITC) is positive control group, the groups treated by MPS-NSSLs-NBD, NSSLs-NBD uncoupled with SP-A nanobodies are negative control groups. After inhaled isoflurane, under anesthetic, the experimental groups are respectively injected with equal amount of MPS-NSSLs-SPANb-FITC and NSSLs-SPANb-FITC, the positive control group is injected with 100 μL, SPANb-FITC (the dosage of fluorescent protein is 1 mg/kg) through caudal vein, the negative control groups are respectively injected with equal amount of MPS-NSSLs-NBD and NSSLs-NBD. Immediately start timing as soon as injected, imaging observation of their distribution in nude mice is implemented respectively in 15 min, 1 h, 3 h, 6 h, 8 h after the injection. At the same time, the real-time observation is implemented by small animals living imaging device.

Because the amino acid sequence of lung SP-A nanobodies and that of mouse rSPA are highly homologous (95%), and it is easy to use nude mice for in vivo imaging which shows advantage, the nude mice are used as in vivo targeting testing experimental animals. The experimental result shows that (see FIG. 6), the groups begin to show obvious accumulation in lung in 15 min after injected with FITC labeled MPS-NSSLs-SPANb and NSSLs-SPANb through caudal vein. Even though in 3 h after injection, it would be seen that obvious image of concentration still exists in lung as before. Both of them have no obvious difference in metabolic status after or before drug loading.

Present invention successfully provides a new human lung tissues targeting hormone preparation, wherein, the nanoliposome serves as a carrier, the nanobody against human pulmonary surfactant protein A serves as a specific lung tissue targeting ligand, methylprednisolone sodium succinate serves as a therapy drug. In accordance with present invention, an efficient, stable human lung tissues-active targeting immune nanoliposome, with specific active lung targeting, is prepared.

BRIEF DESCRIPTION OF THE DRAWINGS

FIGS. 1A-1B shows real-time photographs of the nanoliposome of methylprednisolone (MPS-NSSLs) and the nanoliposome of methylprednisolone coupled with nanobodies against human pulmonary surfactant protein A (MPS-NSSLs-SPANb) under Cry-TEM; wherein, FIG. 1A shows MPS-NSSLs (the nanoliposome of methylprednisolone), which is smooth and rounded in appearance with uniform size and there is no adherence with each other; wherein, FIG. 1B shows MPS-NSSLs-SPANb (the nanoliposome of methylprednisolone coupled with SP-A nanobodies), which is smooth and rounded in appearance with uniform size and there is no adherence with each other.

Carboxylic Acid: the liposome with carboxylic acid; EDC:1-ethyl-3-(3-dimethylaminopropyl) carbodiimide; Primary Amine Containing Molecule: SP-A nanobody with amidogen; Amide Bond Formation: the amide bond is formed by amidation; Sulfo-NHS: N-Hydroxysulfosuccinimide sodium salt; Sulfo-NHS Ester Intermediate: the active ester intermediate of N-Hydroxysulfosuccinimide; O-Acylisourea Active Intermediate: activated O-Acylisourea intermediate.

Figure 1A:
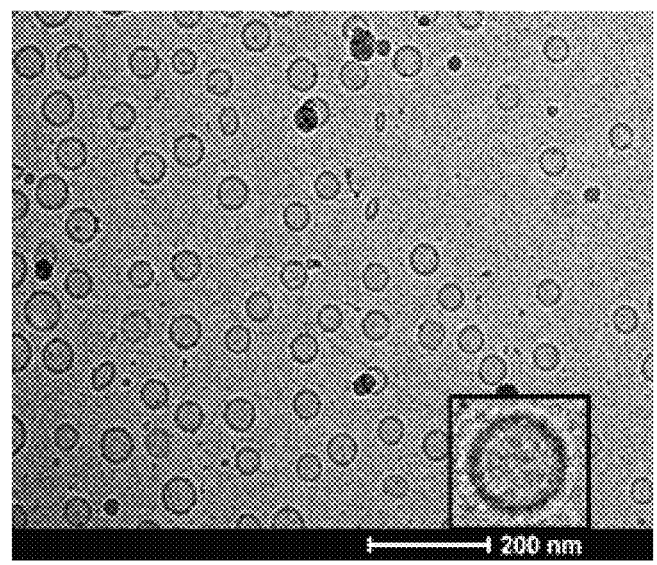
Figure 1B:
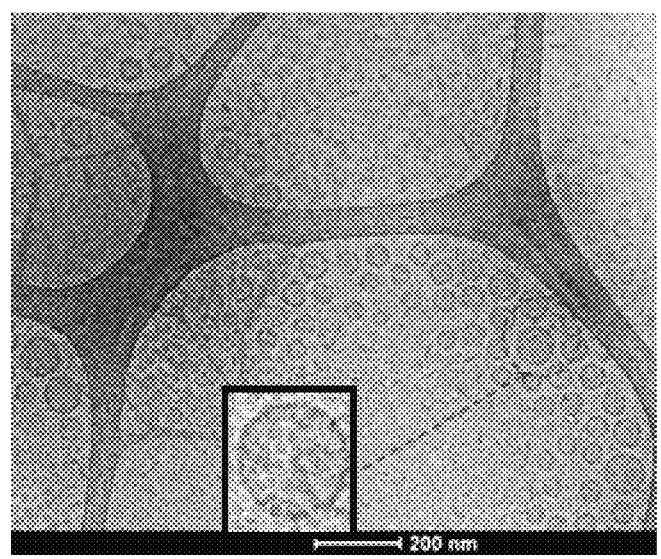
Figure 2A:
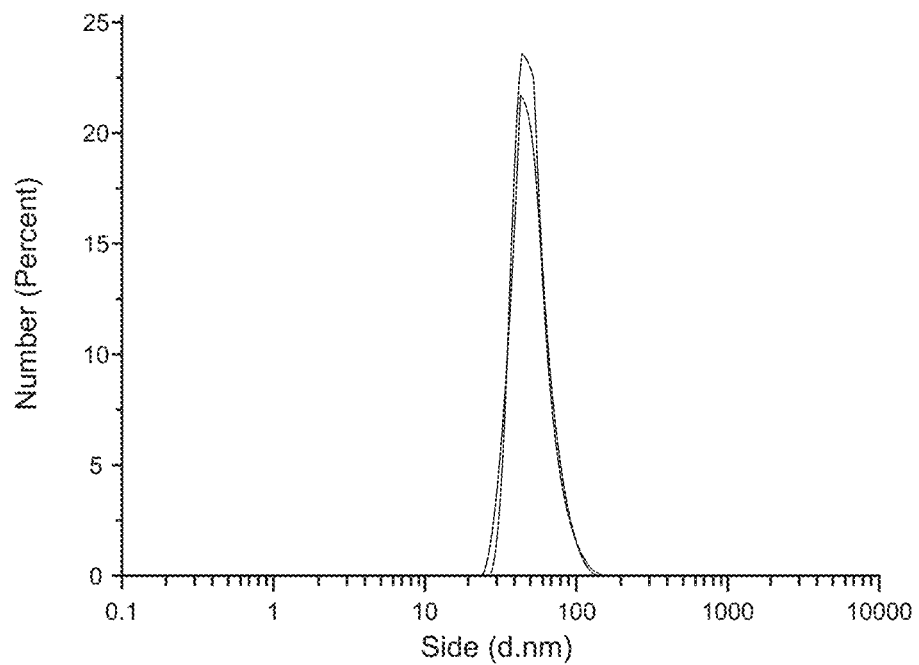
FIGS. 2A-2B shows the particle size distribution of the nanoliposome of methylprednisolone (MPS-NSSLs) and the nanoliposome of methylprednisolone coupled with nanobodies against human pulmonary surfactant protein A (MPS-NSSLs-SPANb) tested by particle size analyzer; wherein, FIG. 2A demonstrates that the average particle size of MPS-NSSLs (the nanoliposome of methylprednisolone) is 108.4±0.4 nm, tested by laser particle analyzer; wherein, FIG. 2B demonstrates that the average particle size of MPS-NSSLs-SPANb (the nanoliposome of methylprednisolone coupled with nanobodies against human pulmonary surfactant protein A) is 119.1±0.2 nm, tested by laser particle analyzer.
Figure 2B:
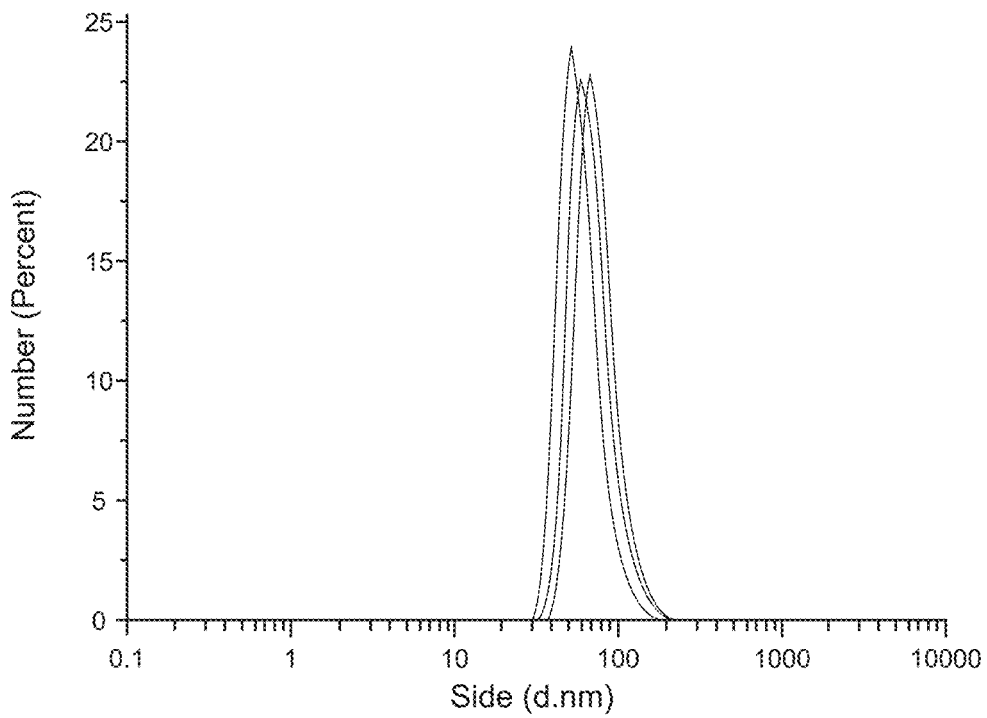
Figure 3:
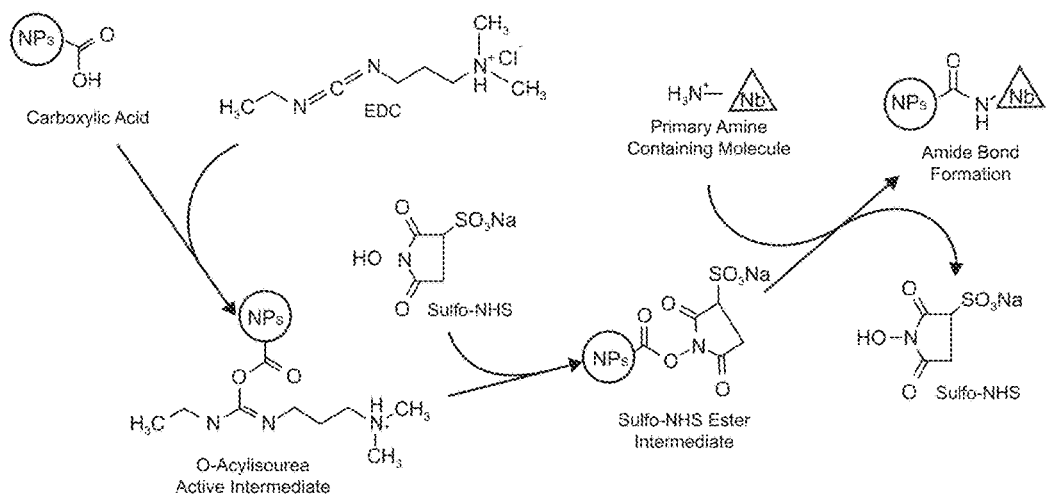
FIG. 3 shows the basic reaction mechanism scheme of coupling the liposome containing DSPE-PEG$_{2000}$-COOH with the amidogen on the surface of the nanobody against human pulmonary surfactant protein A; wherein, the meanings of marks in English are.

As shown in FIG. 3, under the action of EDC (1-ethyl-3-(3-dimethylaminopropyl) carbodiimide), Carboxylic Acid (the liposome with carboxylic acid) activates carboxyl on the surface of the liposome to form unstable O-Acylisourea Active Intermediate (activated O-Acylisourea intermediate), then it forms stable Sulfo-NHS Ester Intermediate (the active ester intermediate of N-Hydroxysulfosuccinimide) under the action of Sulfo-NHS (N-Hydroxysulfosuccinimide sodium salt). Subsequently, this kind of stable intermediate would react with primary amine on SP-A nanobody and the stable Amide Bond has been formed, thus coupling the liposome with the SP-A nanobody has been accomplished.

Figure 4:
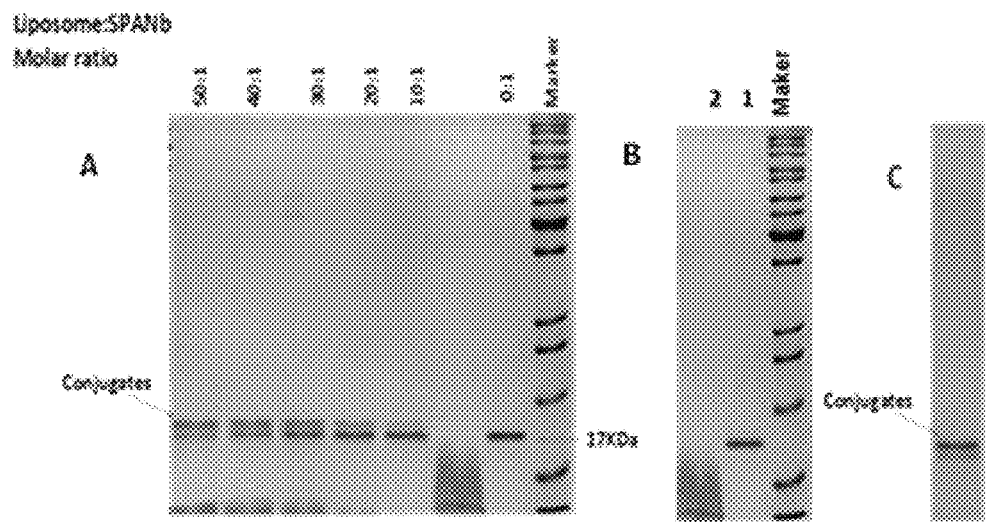

FIGS. 4A-4C shows that SDS-PAGE verification of whether successfully coupling the nanobody against human pulmonary surfactant protein A with the nanoliposome of methylprednisolone; wherein, FIG. 4A is a SD-PAGE photograph of the liposome and human lung SP-A nanobody in different reaction ratio; wherein, 1 in FIG. 4B demonstrates SP-A nanobody positive control, whose molecular mass is 17 KDa, and 2 in FIG. 4B the liposome negative control; FIG. 4C is a SDS-PAGE photograph after coupled the liposome with the SP-A nanobody, wherein, it is able to see an emerging protein band (see the arrow) on the original protein band indicator paper of human lung SP-A nanobody, which means that the nanoliposome of methylprednisolone has successfully coupled with the nanobody against human pulmonary surfactant protein A.

Figure 5:
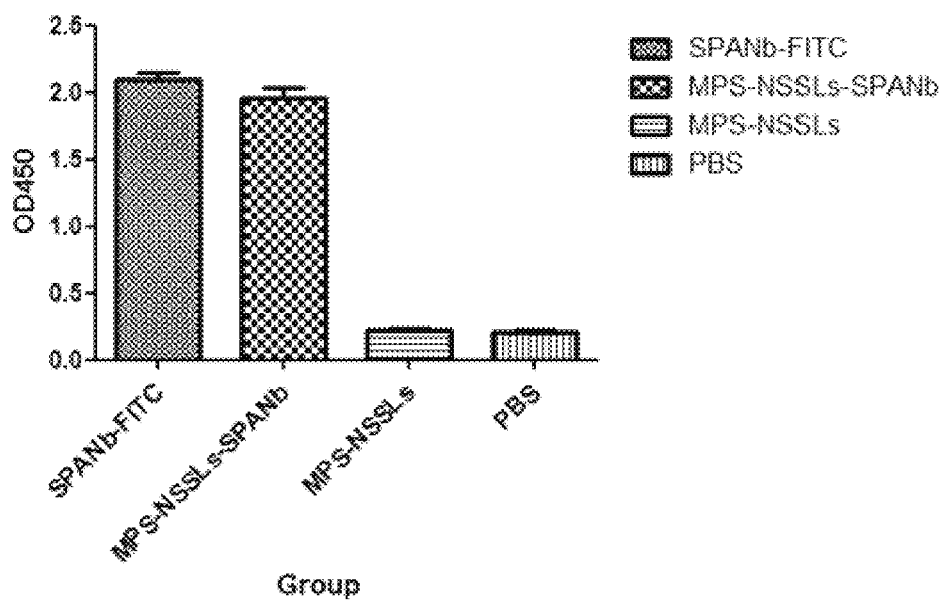

FIG. 5 shows the binding activity of the nanoliposome of methylprednisolone coupled with nanobodies against human pulmonary surfactant protein A and human pulmonary surfactant protein A by ELISA detection; wherein, the meanings of marks in English are:

SPANb-FITC: FITC labeled human lung SP-A nanobody; MPS-NSSLs-SPANb-FITC: FITC labeled human lung targeting nanoliposome of methylprednisolone; MPS-NSSLs: the nanoliposome of methylprednisolone; PBS: phosphate buffer solution.

As shown in FIG. 5, the result from indirect ELISA detection demonstrates that the nanoliposome of methylprednisolone coupled with human lung SP-A nanobodies has better activity for binding to the human pulmonary surfactant protein A as antigens compared with simple nanoliposome of methylprednisolone (MPS-NSSLs-SPANb-FITC), p<0.05; the nanoliposome of methylprednisolone coupled with human lung SP-A nanobodies has little difference of activity for binding to the human pulmonary surfactant protein A as antigens from nanobodies against human pulmonary surfactant protein A (SPANb-FITC), p>0.05. However, there exist statistical differences (P<0.01) while comparing groups of MPS-NSSLs liposome without connecting any targeting antibody, PBS and human lung SP-A nanobody, and all of them do not have reactivity with human lung SP-A antigen.

Figure 6:
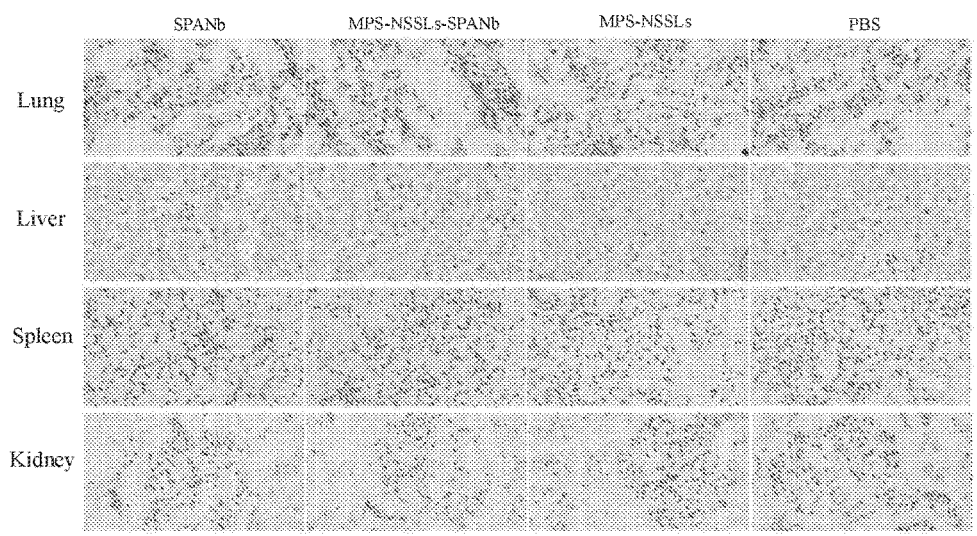

FIG. 6 shows verification of human lung tissues targeting of the nanoliposome of methylprednisolone coupled with nanobodies against human pulmonary surfactant protein A (MPS-NSSLs-SPANb) by immunohistochemical staining; wherein, the meanings of marks in English are:

SPANb: human lung SP-A nanobody; MPS-NSSLs-SPANb: human lung targeting the nanoliposome of methylprednisolone; MPS-NSSLs: the nanoliposome of methylprednisolone; PBS: phosphate buffer solution.

As shown in FIG. 6, fresh lung tissues and organs are used as targets for immunohistochemistry staining. It turned out that both the nanobodies against human pulmonary surfactant protein A (SPANb) and the nanoliposome of methylprednisolone coupled with human lung SP-A nanobodies have been obviously combined with human lung tissues (shown in brown), compared to simple nanoliposome of methylprednisolone (MPS-NSSLs-SPANb), while it is difficult to observe combination of groups of the liposome of methylprednisolone without connecting any targeting antibody (MPS-NSSLs) and PBS with human lung tissues. Wherein, the combining capacity of MPS-NSSLs-SPANb is similar to that of SPANb. However, it is not observed that any of them is obviously combined with human liver, spleen and kidney tissues. As a result, we can find that MPS-NSSLs-SPANb possesses specificity for lung targeting.

Figure 7:
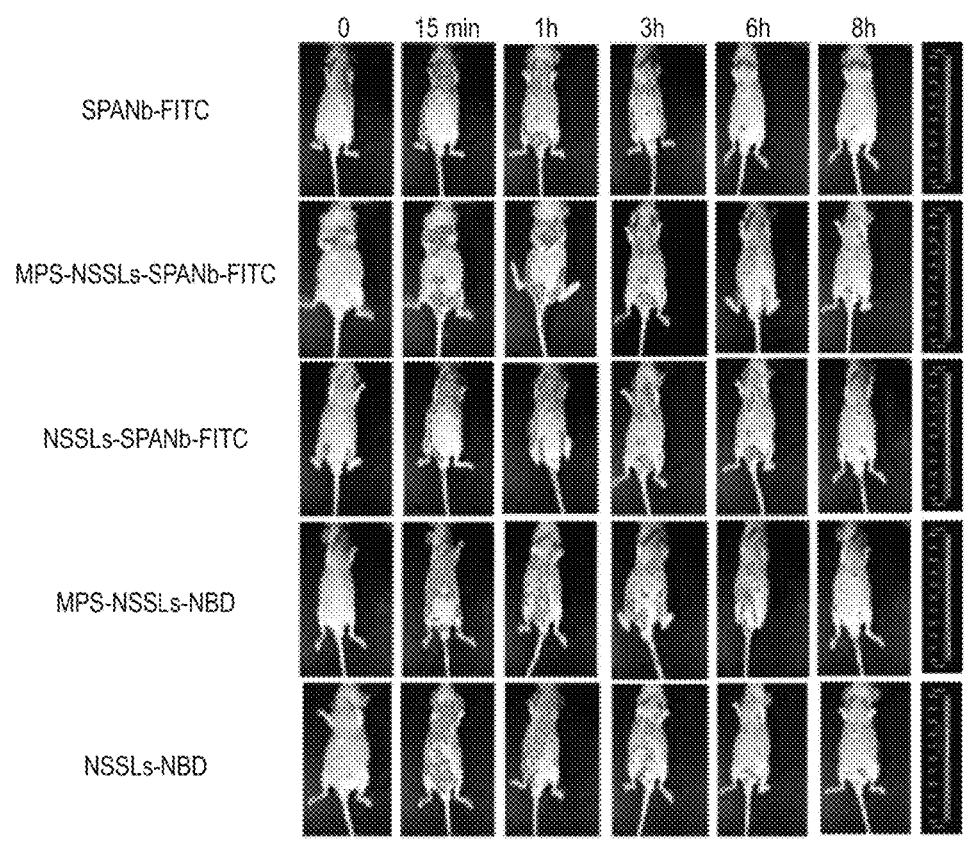

FIG. 7 shows living imaging of small animals treated with different drugs; wherein, the meanings of marks in English are:

SPANb-FITC: FITC fluorescently labeled SP-A nanobody; MPS-NSSLs-SPANb-FITC: fluorescently labeled nanoliposome of methylprednisolone coupled with SP-A nanobodies; NSSLs-SPANb-FITC: fluorescently labeled unloaded nanoliposomes coupled with SP-A nanobodies; MPS-NSSLs-NBD: fluorescently labeled nanoliposome of methylprednisolone; NSSLs-NBD: fluorescently labeled unloaded nanoliposomes.

The result from living imaging of small animals treated with different drugs demonstrates that the groups begin to show obvious accumulation in lung in 15 min after injected with FITC labeled SPANb and MPS-NSSLs-SPANb through caudal vein. Even though in 3 h after injection of SPANb and in 6 h after injection of MPS-NSSLs-SPANb, it would be seen that obvious image of concentration still exists in lung as before. Both of them have no obvious difference in metabolic status after or before drug loading.

DETAILED DESCRIPTION

Present invention provides a human lung tissues-active targeting immune nanoliposome of methylprednisolone, the nanoliposome loaded with therapy drugs are covalently coupled with nanobodies against human pulmonary surfactant protein A; wherein, the therapy drug is methylprednisolone sodium succinate, the nanoliposome comprises phospholipids, cholesterols and long cycling materials. The molar ratio of the methylprednisolone sodium succinate to phospholipids within the nanoliposome is 0.30-0.45.

Present invention further provides a method for producing the human lung tissues-active targeting immune nanoliposome of methylprednisolone, comprising the steps of:

Step 1: A film-ultrasonic technique is employed for preparing the nanoliposome loaded with methylprednisolone sodium succinate, using phospholipid, cholesterol, DSPE-PEG, DSPE-PEG$_{2000}$-COOH as film-forming materials;

Step 2: the nanoliposome loaded with methylprednisolone sodium succinate prepared by Step 1 is covalently coupled with nanobodies against human pulmonary surfactant protein A.

Present invention is further illustrated using the following embodiments, but any of the embodiments or its combinations thereof should not be construed as a limitation to the scope of present invention.

EXAMPLE

1. Preparation of the Nanoliposome of Methylprednisolone (MPS-NSSLs)

A film-ultrasonic technique is employed for preparing the nanoliposome of methylprednisolone. The mixed solvent of chloroform/methanol (the volume ratio is 2:1) is used to dissolve respectively weighed distearoyl phosphatidylcholine (DSPC), cholesterol and DSPE-$PEG_{2000}$(the molar ratio of each component is 20:14.5:1.8) with formula dosage in a round-bottom flask. After dried under nitrogen, a membrane with even thickness glued to the wall of the round-bottom flask is formed. The membrane is vacuum dried overnight at room temperature, for removing any organic solvent. A moderate amount of calcium acetate solution (concentration is 200 mM) is used for hydration, then an ultrasound bath in 72° C. is used to dissolve lipidosomes (ultrasonic processing in 30 mins, with ultrasonic power of 250 W), thus mid blue opalescence solution is obtained. Sequentially, the ultrasound-treated hydration solution runs through three filter membranes with pore size of 0.4 μm, 0.2 μm, 0.1 μm in sequence, by means of the Lipidosome Extruder (Avanti® Mini-Extruder), extruded 13-17 times in each level, and then lipidosome suspension is obtained. The obtained lipidosome suspension is dialyzed in the dialysis tube (molecular weight of 300 kDa) containing 0.9% normal saline overnight. Methylprednisolone sodium succinate (MPS) with formula dosage is weighed and dissolved in 0.9% normal saline for preparing MPS solution with molarity of 4.2 mM. The MPS solution is mixed with the lipidosome suspension (concentration of phospholipids is 14.3 mM), then the mixture is heated in water bath at 70° C. for 40 mins, at last, it is stored at 4° C. Free MPS, which is not encapsulated, is removed with the help of gel filtration chromatography (Superose G-25).

2. Characterization of the Nanoliposome of Methylprednisolone

1) Morphologic Observation

A moderate amount of liposome suspension is treated with liquid nitrogen quick freezing, and the appearance of the nanoliposome of methylprednisolone in the liposome suspension could be observed by Cry-TEM. We can see that they show entirely spherical in shape, with even size (see FIG. 1A).

2) Determination of Particle Size

After a moderate amount of liposome suspension diluted with appropriate distilled water, the diluted liposome suspension is put into a sample pool, then the particle size of samples are automatically scanned. The average particle size of the nanoliposome of methylprednisolone is 108.4±0.4 nm (see FIG. 2A).

3) Entrapment Efficiency Determination

HPLC is used to detect the concentration of methylprednisolone sodium succinate. Standard curve: Y=23461X-5367.2 and correlation coefficient: $R^2$=0.9999 indicate good linear relation (the range of methylprednisolone sodium succinate is 1~200 $\mu g \cdot ml^{-1}$) of the concentration (X) and peak area ratio (Y). The entrapment rate of the nanoliposome of methylprednisolone to methylprednisolone sodium succinate is 90.1±0.32%.

3. Preparation of the Nanoliposome of Methylprednisolone Coupled with Nanobodies Against Human Pulmonary Surfactant Protein A (MPS-NSSLs-SPANb)

Firstly, the liposome containing DSPE-$PEG_{2000}$-COOH is prepared, and the carboxyl on the surface of the liposome is utilized to make coupling reaction with amidogens in nanobodies against human pulmonary surfactant protein A (FIG. 3 shows the reaction process).

A film-ultrasonic technique is employed for using phospholipid, cholesterol, DSPE-$PEG_{2000}$, DSPE-$PEG_{2000}$-COOH as film-forming materials to prepare the nanoliposome of methylprednisolone containing DSPE-$PEG_{2000}$-COOH. The preparation process of it is the same as the preparation process of the nanoliposome of methylprednisolone containing MPS-NSSLs.

An aqueous solution of 120 μL 0.25 mol/L 1-ethyl-3-(3-dimethylaminopropyl) carbodiimide (EDC) and 120 μL 0.25 mol/L N-hydroxysulfosuccinimide (S-NHS) is added into 150 μL liposome suspension (MES buffer solution, pH 4-5.5, total molar quantity of the liposome is 3 μmol) containing DSPE-$PEG_{2000}$-COOH.

The mixture is incubated for 15 min at room temperature, then using NaOH to neutralize to pH 7.5.

The nanobody against human pulmonary surfactant protein A is added to the activated liposome and blended (the molar concentration ratio of DSPE-$PEG_{2000}$-COOH and the nanobody against human pulmonary surfactant protein A is 70: 1). The obtained mixture is stirred gently at 4° C. and keeps the temperature, reacting for 8 h. Sepharose CL-4B column pretreated by buffer solution is used to separate the immune liposome from unconnected antibody.

1) Morphologic Observation

A moderate amount of liposome suspension is treated with liquid nitrogen quick freezing, and the appearance of the nanoliposome of methylprednisolone in the liposome suspension could be observed by Cryo-TEM. We can see that they show entirely spherical in shape, with even size (see FIG. 1B).

2) Determination of Particle Size

After a moderate amount of liposome suspension diluted with appropriate distilled water, the diluted liposome suspension is put into a sample pool, then, the particle size of samples are automatically scanned. The average particle size of the nanoliposome of methylprednisolone coupled with nanobodies against human pulmonary surfactant protein A is 119.1±0.2 nm (see FIG. 2B).

3) Entrapment Efficiency Determination

HPLC is used to detect the concentration of methylprednisolone sodium succinate. Standard curve: Y=23461X-5367.2 and correlation coefficient: $R^2$=0.9999 indicate good linear relation (the range of methylprednisolone sodium succinate is 1~200 $\mu g \cdot ml^{-1}$) of the concentration (X) and peak area ratio (Y). The entrapment rate of the nanoliposome of methylprednisolone to methylprednisolone sodium succinate is 89.7±0.1%.

4) Stability Detection

The nanoliposome of methylprednisolone coupled with nanobodies against human pulmonary surfactant protein A is stored for 12 weeks at 4° C., but the entrapment rate of the liposome to methylprednisolone sodium succinate has no significant changes (p>0.05) during detection, which means that it has good stability (see Table 1).

4. Verification of Whether Successfully Coupling the Nanobody Against Human Pulmonary Surfactant Protein A with the Nanoliposome of Methylprednisolone The polyacrylamide gel electrophoretic analysis (SDS-PAGE) of the nanoliposome of methylprednisolone coupled with nanobodies against human pulmonary surfactant protein A shows that the nanoliposome of methylprednisolone has successfully coupled with human pulmonary surfactant protein A, because of the increasing of molecular mass which equals to the original molecular mass of human pulmonary surfactant protein A added the molecular mass of the liposome (see FIG. 4).

After nanobodies against human pulmonary surfactant protein A coupled with the nanoliposome of methylprednisolone, Sepharose CL-4B column purification is applied. Then, the human pulmonary surfactant protein A as antigens is used for ELISA detection technology, which shows that the nanoliposome of methylprednisolone coupled with nanobodies against human pulmonary surfactant protein A has better activity for binding to the human pulmonary surfactant protein A as antigens compared with simple nanoliposome of methylprednisolone, p<0.05; the nanoliposome of methylprednisolone coupled with nanobodies against human pulmonary surfactant protein A has little difference of activity for binding to the human pulmonary surfactant protein A as antigens from nanobodies against human pulmonary surfactant protein A, p>0.05 (see FIG. 5).

5. Human Lung Tissues Targeting Test of the Immune Nanoliposome of Methylprednisolone (MPS-NSSLs-SPANb) Coupled with Nanobodies Against Human Pulmonary Surfactant Protein A Fresh lung tissues and organs are used as targets for immunohistochemistry staining. It turned out that both the nanobodies against human pulmonary surfactant protein A and the nanoliposome of methylprednisolone coupled with nanobodies against human pulmonary surfactant protein A have been obviously combined with human lung tissues (shown in brown), wherein, the combining capacity of the nanoliposome of methylprednisolone coupled with nanobodies against human pulmonary surfactant protein A is similar to that of the nanobodies against human pulmonary surfactant protein A. However, it is not observed that any of them is obviously combined with human liver, spleen and kidney tissues. As a result, we can find that the nanoliposome of methylprednisolone coupled with nanobodies against human pulmonary surfactant protein A possesses specificity for lung targeting (see FIG. 6).

6. Living Imaging of Small Animals for Real-Time Observation of Metabolism of MPS-NSSLs-SPANb In Vivo 5 nude mice in 2 weeks old are selected and divided into five groups, wherein, the group treated by the lung targeting liposome of methylprednisolone (MPS-NSSLs-SPANb-FITC) and the group treated by the lung targeting liposome without loading drugs (NSSLs-SPANb-FITC) are experimental groups, the group treated by FITC labeled lung SP-A nanobodies (SPANb-FITC) is positive control group, the groups treated by MPS-NSSLs-NBD, NSSLs-NBD uncoupled with SP-A nanobodies are negative control groups. After inhaled isoflurane, under anaesthetic, the experimental groups are respectively injected with equal amount of MPS-NSSLs-SPANb-FITC and NSSLs-SPANb-FITC, the positive control group is injected with 100 μL, SPANb-FITC (the dosage of fluorescent protein is 1 mg/kg) through caudal vein, the negative control groups are respectively injected with equal amount of MPS-NSSLs-NBD and NSSLs-NBD. Immediately start timing as soon as injected, imaging observation of their distribution in nude mice is implemented respectively in 15 min, 1 h, 3 h, 6 h, 8 h after the injection. At the same time, the real-time observation is implemented by small animals living imaging device.

Because the amino acid sequence of lung SP-A nanobodies and that of mouse rSPA are highly homologous (95%), and it is easy to use nude mice for in vivo imaging which shows advantage, the nude mice are used as in vivo targeting testing experimental animals. The experimental result shows that (see FIG. 6), the groups begin to show obvious accumulation in lung in 15 min after injected with FITC labeled MPS-NSSLs-SPANb and NSSLs-SPANb through caudal vein. Even though in 3 h after injection, it would be seen that obvious image of concentration still exists in lung as before. Both of them have no obvious difference in metabolic status after or before drug loading.

Present invention successfully provides a new human lung tissues targeting hormone preparation, wherein, the nanoliposome serves as a carrier, the nanobody against human pulmonary surfactant protein A serves as a specific lung tissue targeting ligand, methylprednisolone sodium succinate serves as a therapy drug. In accordance with present invention, an efficient, stable human lung tissues-active targeting immune nanoliposome, with specific active lung targeting, is prepared.

Above mentioned specific embodiments of present invention are presented for purposes of illustration and description, but is not intended to be exhaustive or limited to the invention in the form disclosed. Many modifications and variations will be apparent to those of ordinary skill in the art without departing from the scope and spirit of the invention. Thus, equality of changes and modifications without departing from the spirit and scope of the invention shall fall within the scope of the invention.

What is claimed is:

1. A human lung tissues-active targeting immune nanoliposome of methylprednisolone, wherein, nanoliposomes loaded with therapy drugs is covalently coupled with nanobodies against human pulmonary surfactant protein A; wherein, the therapy drug is methylprednisolone sodium succinate, the nanoliposome consists of phospholipids, cholesterols and long cycling materials, and wherein the molar ratio of the methylprednisolone sodium succinate to phospholipids within the nanoliposome is 0.30-0.45.

2. The human lung tissues-active targeting immune nanoliposome of methylprednisolone as claimed in claim 1, wherein, the phospholipid is distearoyl phosphatidylcholine, and wherein the long cycling material is selected from the group consisting of DSPE-PEG$_{2000}$ and DSPE-PEG$_{2000}$-COOH.

3. The human lung tissues-active targeting immune nanoliposome of methylprednisolone as claimed in claim 2, wherein, the final molar ratio of nanobodies against human pulmonary surfactant protein A to DSPE-PEG$_{2000}$-COOH is 1:70; the molar ratio of phospholipids: cholesterols: DSPE-PEG$_{2000}$ is 20:14.5:1.8.

4. The human lung tissues-active targeting immune nanoliposome of methylprednisolone as claimed in claim 1, wherein, the therapy drug is further selected from hydrocortisone, dexamethasone or prednisolone.

5. The human lung tissues-active targeting immune nanoliposome of methylprednisolone as claimed in claim 1, wherein, the nanoliposome is entirely spherical in shape, with average particle size of 119.1±0.2 nm; the entrapment rate of the nanoliposome to active pharmaceutical ingredients in therapy drugs is 89.7±0.1%.

6. The human lung tissues-active targeting immune nanoliposome of methylprednisolone as claimed in claim 1, wherein, the molar ratio of methylprednisolone sodium succinate to the phospholipids within the nanoliposome is 0.40.

7. A method for producing the human lung tissues-active targeting immune nanoliposome of methylprednisolone of claim 1, wherein, the method comprises the steps of:
  Step 1, a film-ultrasonic technique is employed for preparing the nanoliposome loaded with methylprednisolone sodium succinate, using phospholipid, cholesterol, DSPE-PEG$_{2000}$, DSPE-PEG$_{2000}$-COOH as film-forming materials; and
  Step 2, the nanoliposome loaded with methylprednisolone sodium succinate prepared by Step 1 is covalently coupled with nanobodies against human pulmonary surfactant protein A.

8. The method as claimed in claim 7, wherein, the Step 1 further comprises:
  a film-ultrasonic technique is employed for preparing the nanoliposome of methylprednisolone containing DSPE-PEG$_{2000}$-COOH; wherein, the molar ratio of DSPC: cholesterol: DSPE-PEG$_{2000}$: DSPE-PEG$_{2000}$-COOH is 20:14.5:1.8: 0.05.

9. The method as claimed in claim 7, wherein, the Step 2 comprises procedures as follows:
  an aqueous solution of 120 μL 0.25 mol/L 1-ethyl-3-(3-dimethylaminopropyl) carbodiimide and 120 μL 0.25 mol/L N-hydroxysulfosuccinimide is added into 150 μL liposome suspension containing DSPE-PEG2000-COOH; obtained mixture is incubated for 15 min at room temperature, then using NaOH to neutralize to pH 7.5; the nanobody against human pulmonary surfactant protein A is added to the activated liposome and blended, wherein, the molar concentration ratio of DSPE-PEG2000-COOH and the nanobody against human pulmonary surfactant protein A is 70:1; this obtained mixture is stirred gently at 4° C. and keep the temperature, reacting for 8 h; finally, Sepharose CL-4B column pretreated by buffer solution is used to separate the immune liposome from unconnected antibody.

* * * * *